(12) United States Patent
Eastwood

(10) Patent No.: US 10,653,516 B1
(45) Date of Patent: May 19, 2020

(54) ELECTROMAGNETIC ARTIFICIAL MUSCLE

(71) Applicant: Gov of the United States, as rep. by US Air Force, Wright-Patterson AFB, OH (US)

(72) Inventor: Matthew A Eastwood, Travis AFB, CA (US)

(73) Assignee: The Government of the United States as Represented by the Secretary of the Air Force, Wright-Patterson AFB, OH (US)

( * ) Notice: Subject to any disclaimer, the term of this patent is extended or adjusted under 35 U.S.C. 154(b) by 30 days.

(21) Appl. No.: 16/043,672

(22) Filed: Jul. 24, 2018

(51) Int. Cl.
- *A61F 2/08* (2006.01)
- *A61F 2/68* (2006.01)
- *B25J 9/10* (2006.01)
- *A61F 2/70* (2006.01)

(52) U.S. Cl.
CPC .................. *A61F 2/08* (2013.01); *A61F 2/68* (2013.01); *B25J 9/1075* (2013.01); *A61F 2002/0894* (2013.01); *A61F 2002/6863* (2013.01); *A61F 2002/705* (2013.01)

(58) Field of Classification Search
CPC ............... A61F 2/08; A61F 2002/0894; A61F 2002/6863; B25J 9/1075; B25J 9/12
See application file for complete search history.

(56) References Cited

U.S. PATENT DOCUMENTS

| | | | | |
|---|---|---|---|---|
| 4,819,547 A * | 4/1989 | Kukolj | .................. | F15B 15/103 92/153 |
| 6,168,634 B1 * | 1/2001 | Schmitz | ................. | B25J 9/1075 414/4 |
| 6,223,648 B1 * | 5/2001 | Erickson | ............... | F15B 15/103 92/92 |
| 8,395,466 B2 * | 3/2013 | Zhao | ...................... | B25J 9/1075 335/229 |
| 9,662,197 B2 * | 5/2017 | Yun | ........................... | A61F 2/08 |
| 2019/0083230 A1 * | 3/2019 | Lizzio | ....................... | A61F 2/08 |

\* cited by examiner

*Primary Examiner* — Bruce E Snow
(74) *Attorney, Agent, or Firm* — AFMCLO/JAZ

(57) ABSTRACT

An artificial muscle including an internal electromechanically charged rod extending beyond two attach points. A plurality of mesh cylinders having a mesh cylinder top and a mesh cylinder bottom surrounding the charged rod. A fiber surrounding the mesh cylinders and mechanically attached to the mesh cylinders at an attachment spacing and wherein an electromagnetic source activates the artificial muscle through at least one microprocessor. The artificial muscle fiber may be nylon and the attach points may be titanium. The artificial muscle fiber may be coated with nylon. The artificial muscle fiber may contain a viscous fluid.

8 Claims, 1 Drawing Sheet

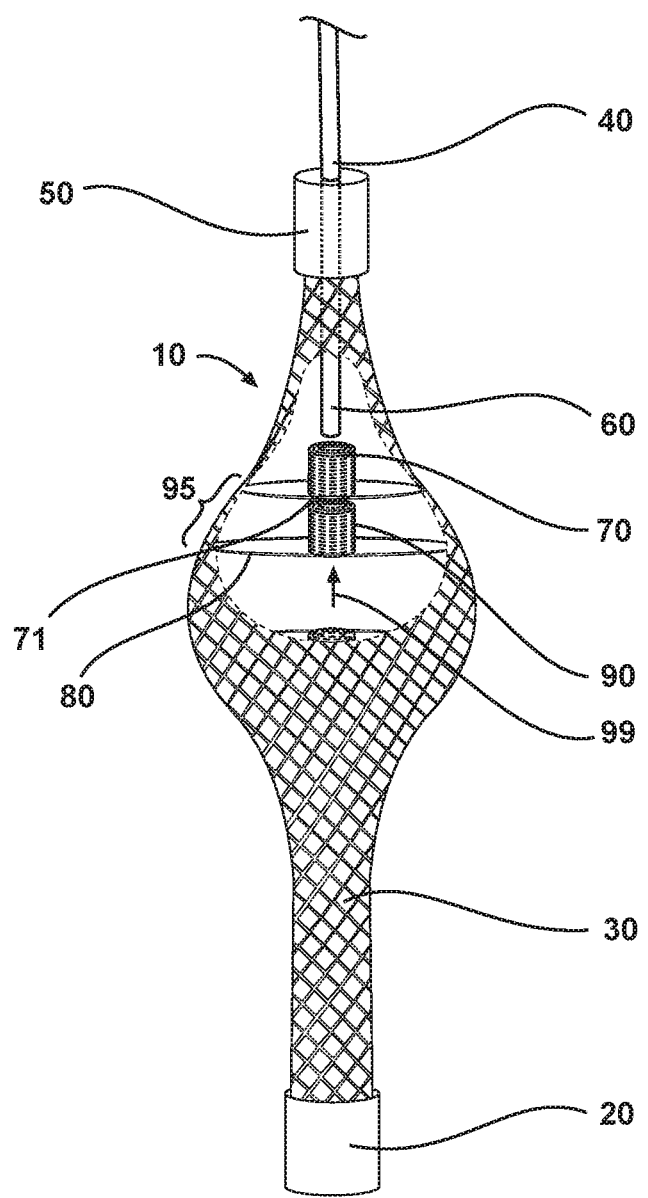

ELECTROMAGNETIC ARTIFICIAL MUSCLE

RIGHTS OF THE GOVERNMENT

The invention described herein may be manufactured and used by or for the Government of the United States for all governmental purposes without the payment of any royalty.

FIELD OF THE INVENTION

The present invention relates generally to mobility and, more particularly, to replacement of muscle fibers with synthetic implants with electromechanical/electromagnetic and mechanical operation supporting synthetic muscle movement.

BACKGROUND OF THE INVENTION

Currently, throughout the world there are many whom due to trauma, cancer and other disorders such as muscular dystrophy, do not have the strength or mobility. Additionally prosthesis is typically used for amputated limbs. The present invention provides a way to provide a more complete augmentation of the skeletal muscles. While researchers have been working by heating polymer weaves with a high voltage electric current to that coil the filaments into a helix creating a pulling force, there are however limitations overcome by the present invention.

SUMMARY OF THE INVENTION

The present invention overcomes the foregoing problems and other shortcomings, drawbacks, and challenges of the prior art in designing a replacement electromechanical muscle replacement. While the invention will be described in connection with certain embodiments, it will be understood that the invention is not limited to these embodiments. To the contrary, this invention includes all alternatives, modifications, and equivalents as may be included within the spirit and scope of the present invention. According to one embodiment of the present invention, disclosed is an artificial muscle including an internal electromechanically charged rod extending beyond two attach points. A plurality of mesh cylinders having a mesh cylinder top and a mesh cylinder bottom surrounding the charged rod. A fiber, material or mesh of fibers surrounding the mesh cylinders and mechanically attached to the mesh cylinders at an attachment spacing and wherein an electromagnetic source activates the artificial muscle through at least one microprocessor. The artificial muscle fiber may be nylon and the attach points may be titanium. The artificial muscle fiber may be coated with nylon. The fiber material or mesh of fibers surrounding the mesh cylinders contains a viscous fluid around the mesh cylinders.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

FIG. 1 is an exploded semitransparent illustration of one embodiment of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

The present invention improves the flexibility of an artificial muscle 10 through the use of scaffolding of the fiber consisting of wrapped fabric preferably in a polymer fiber. The artificial muscle 10 has a first point of attachment 20 and a second point of attachment 50. One or both of the points of attachment may include an electromagnetically charged wire (or pole) 40 either attached to the attach point or going through the attach point as shown in FIG. 1, second attach point 50 as a means for electromagnetic activation inducing mechanical motion.

In one embodiment the first point of attachment 20 and the second point of attachment 50 may be made of titanium or any other material known in the art. The first point of attachment 20 and or the second point of attachment 50 serve as a point of attachment between a fiber material (fiber)/mesh of fibers 30 and a subjects bone or tendon (not shown). Titanium provides a low conduction of magnetic energy and lower rates of rejection from the body, which may be desirable in some applications.

In one embodiment the fibers 30 may be made from nylon or any material known in the art. In one embodiment nylon may provide flexibility and resist absorption into its surroundings when deployed into a patient's body.

In one embodiment the fibers 30 are weaved into a finger-trap configuration with the ends terminating at the titanium attachment points (20, 50). In one attachment may improve stretching, bowing and overall strength.

In one embodiment the fibers 30 may be coated with a coating (not shown). The coating may be Teflon or any material known in the art that has antifriction properties and magnet insulation properties, allowing easy gliding of the fibers past other fibers and isolating a magnetic field (not shown).

Within fibers 30 weave may be a plurality of mesh cylinders 90. The fibers may be impermeable such that contain a viscous fluid which dampens magnetic movement of the mesh cylinders 90. In one embodiment the mesh cylinders 90 are stainless steel or any material known in the art that will react to a magnetic field. In one embodiment the mesh cylinders 90 may be attached by a plurality of connector(s) 80 to the fibers 30 and suspended along the artificial muscle 10. In one embodiment the attachment is optimized at key points in the structure to maximize the strength and efficacy of the magnetic pull. In one embodiment the mesh cylinder has a mesh cylinder top 70. The mesh cylinder top 70 may be a mesh and in one embodiment exposed directly to an electromagnetic charges wire/pole 40. In one embodiment the tops are mesh and uncoated to connect to the electromagnetic wire/pole 40 within one or more point of attachment 20, 50. In one embodiment the mesh cylinder bottom 71 may similarly be exposed directly to an electromagnetic wire 60 inside the artificial muscle 10, wherein the bottoms 71 are mesh and uncoated to connect to the electromagnetic wire/pole 40 within one or more point of attachment 20. As shown in FIG. 1 the electromechanical wire/pole 40 and the electromechanical wire 60 may be one piece. In one embodiment the entire inner surface (not shown) of mesh cylinder 90 may be exposed directly to an electromagnetic wire 60 wherein the cylinder inner surface are mesh and uncoated to connect to the electromagnetic wire/pole 40. In on embodiment, only electromechanical wire 60, or a portion thereof is electromechanically charged. In one embodiment the artificial muscle mesh cylinders may surround the charged rod and move over the charge rod surface to further extend or retract the artificial muscle.

The plurality of cylinders 90 may In one embodiment connect to via chain reaction to adjacent cylinders and permit viscous fluids to slow or dampen the reaction due to their mesh structure which allows a fluid (not shown) to be contained within the fiber 30. In one embodiment the connectors 80 may be between the fibers 30 and the cylinders 90 with a plurality of eyelets such as polished or any attachment mechanism known in the art that may mitigate fiber 30 breakage from contact with the mesh cylinder 90. In one embodiment the fiber coating may keep the pole 60 generated magnetic field (not shown) from pulling the mesh cylinders in unintended directions, in one embodiment keeping the magnetic force exerted on the mesh cylinder linear. The fiber surrounding the mesh cylinders may be designed to hold a viscous fluid around the mesh cylinders, and between the first point of attachment 20 and a second point of attachment 50.

The Teflon may act as an insulator keeping the interfering magnetic fields from other fiber(s) from pulling in unintended directions keeping the motion as linear as possible in the Direction of Pull 99 in FIG. 1. The degree of artificial muscle 10 control may be influenced by the design choice of fiber 30, cylinder 90 and connectors 80. In one embodiment a direction of pull may also be in the opposite direction of pull 99 (not shown), or alternatively in both the direction of pull 99 and the opposite direction of pull (not shown).

Additionally, staggering or even chains of these fibers can control the degree of movement by interfacing with microprocessors and myoelectric sensors. Battery sources for the electromagnetic source for these fibers transmitted through the skin using induction-charging technology. In one embodiment an attach point spacing 95 may be used to control the degree of artificial muscle control and degree of movement. The pull force is being exerted on at least one of a plurality of mesh cylinders 90. In one embodiment the magnetic force in transferable from one mesh cylinder to an adjacent mesh cylinder through the plurality of mesh cylinders as needed for the desired function/movement. In one embodiment the viscous fluid contained by the fiber(s) around the mesh cylinders may dampen the movement of the mesh cylinders to provide a preferred and/or gradual muscle movement.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. An artificial muscle including:
   an internal electromechanically charged rod moveably extending between a first attach point and a second attach point;
   a plurality of mesh cylinders having a mesh cylinder top and a mesh cylinder bottom;
   a plurality of fibers surrounding the mesh cylinders having a plurality of connectors mechanically connecting the fibers to the mesh cylinders and wherein
   an electromagnetic source activates the artificial muscle through at least one microprocessor to electromechanically create a mesh cylinder movement.

2. The artificial muscle of claim 1 wherein the fibers are nylon and the attach points are titanium.

3. The artificial muscle of claim 2 wherein the fibers are weaved into a finger-trap configuration having a first end attached to a first point of attachment and a second end attached to a second point of attachment.

4. The artificial muscle of claim 1 wherein the fibers are coated with nylon.

5. The artificial muscle of claim 1 wherein the mesh cylinder movement is dampened by a viscous fluid contained around the mesh cylinders by the fibers.

6. The artificial muscle of claim 1 wherein the electromagnetic source is transmitted using induction-charging.

7. The artificial muscle of claim 1 wherein the plurality of connectors have an attach point spacing to control the degree of the mesh cylinder movement.

8. The artificial muscle of claim 1 wherein the mesh cylinders may surround the charged rod and move over a charge rod surface further extend or retract the artificial muscle.

* * * * *